(12) United States Patent
Chae et al.

(10) Patent No.: US 6,706,888 B2
(45) Date of Patent: Mar. 16, 2004

(54) PROCESSES FOR PREPARING IMIDAZOLE DERIVATIVES AND SALTS THEREOF

(75) Inventors: Jeong-Seok Chae, Seoul (KR); Tai-Au Lee, Seoul (KR); Sang-Seon Park, Anyang (KR); Doo-Byung Lee, Seoul (KR); Beom-Joo Maeng, Ansan (KR)

(73) Assignee: Yuhan Corporation, Seoul (KR)

( * ) Notice: Subject to any disclaimer, the term of this patent is extended or adjusted under 35 U.S.C. 154(b) by 0 days.

(21) Appl. No.: 10/359,057

(22) Filed: Feb. 6, 2003

(65) Prior Publication Data

US 2003/0153769 A1 Aug. 14, 2003

(30) Foreign Application Priority Data

Feb. 8, 2002 (KR) ...................................... 10-2002-7231

(51) Int. Cl.$^7$ ........................................... C07D 233/54
(52) U.S. Cl. .................................................. 548/341.1
(58) Field of Search ...................................... 548/341.1

(56) References Cited

FOREIGN PATENT DOCUMENTS

| WO | WO 97/18813 | 5/1997 |
| WO | WO 99/27928 | 6/1999 |
| WO | WO 99/28314 | 6/1999 |
| WO | WO 00/23438 | 4/2000 |
| WO | WO 00/53596 | 9/2000 |
| WO | WO 01/09128 | 2/2001 |

OTHER PUBLICATIONS

Pfister et al., 1981, "A short synthesis of 5–methylhistamine", J. Heterocyclic Chem., 18:831–832.*
Kivits et al., 1975, "A convenient preparation of 3–(1H–imidazol–4–yl)propanol", Heterocyclic Chem., 12:577.*
H. Stark et al; "Jodoproxyfan and Related Compounds: A Reversible Radiogland and Novel Classes of Antagonists With High Affinity and Selectivity for the Histamine $H_3$ Receptor"; J. Med. Chem.; 1996; pp. 1220–1226.
G. Kivits et al; "A Convenient Preparation of 3–(1H–Imidazol–4–YL)Propanol"; Heterocyclic Chem.; Jun. 1975; p. 577.
J. Pfister et al; "A Short Synthesis of 5–Methylhistamine (1)"; J. Heterocyclic Chem.; Jun. 1981; pp. 831–832.
Shunack et al; "Ather Un Ester Des 4–(2–Hydroxyaethyl)–Imidazols Und Ester Der 4–Imidazolpropionsaure"; Arch. Pharm.; 1974, pp. 517 to 523.
S. Fox et al; "Thiamine Analogs. IV 4(5)–Methyl–5(4)–(β–Hydroxyethyl)–Imidazole"; J. Am. Chem. Soc.; 1945, pp. 496 to 497.
C. Marzabadi et al: "Stereoselective Glucal Epoxide Formation"; J. Org. Chem.; 1993; pp. 3761 to 3766.
A. Bechwith et al; "The Mechanism of the β–Acyloxyalkyl Radical Rearrangement. Part 2: β–Acyloxytetrahydropyranyl Radicals"; J. Org. Chem.; 1993; pp. 1673 to 1679.
E. Gaydou; "Action Des N–Haloimides Sur Les Ethers D'Enols Reactions En Milieu Protique"; Tetrahedron Letters No. 40; 1992; pp. 4005 to 4058.
M. Smietana et al; "An Improved Synthesis of Iodohydrins From Alkenes"; Tetrahedron Letters No. 41; 2000; pp. 193 to 195.
J. Shelton et al; "Reaction on N–Bromosuccinimide with Dihydropyran"; J. Org. Chem.; Jan. 14, 1958; pp. 1128 to 1133.

* cited by examiner

*Primary Examiner*—Joseph K. McKane
*Assistant Examiner*—Robert Shiao
(74) *Attorney, Agent, or Firm*—Lowe Hauptman Gilman & Berner LLP

(57) ABSTRACT

The present invention provides a process for preparing an imidazole derivative or its salt which comprises reacting a tetrahydrofuran or tetrahydropyran derivative with formamidine or its salt in the presence of a base.

12 Claims, No Drawings

PROCESSES FOR PREPARING IMIDAZOLE DERIVATIVES AND SALTS THEREOF

This application is based upon and claims priority from Korean Patent Application No. 2002-7231 filed Feb. 8, 2002, the contents of which are incorporated herein by reference.

BACKGROUND OF THE INVENTION

1. Field of the Invention

The present invention relates to a process for preparing an imidazole derivative or its salt, which is useful as an intermediate for the preparation of an anti-viral, an anti-fungal or an anti-cancer agent.

2. Description of the Related Art

An imidazole derivative, more specifically a 4(5)-hydroxyalkyl imidazole derivative, or its salt is useful as an intermediate for the preparation of an anti-viral, an anti-fungal or an anti-cancer agent (see, WO 99/28314, WO 99/27928, WO 00/23438 and WO 00/53596). For example, 4-(3-hydroxypropyl)-imidazole is a useful intermediate for the preparation of anti-cancer agents (WO 01/09128).

Imidazole derivatives or salts thereof may be prepared by various methods, for example, as disclosed in WO 97/18813; Holger Stark, et al., *J. Med. Chem.*, 1996, 39, 1220; G. A. A. Kivits. et al., *Heterocyclic chem.*, 1975, 12, 577; Jurg R. Pfister et al., *J. Heterocyclic Chem.*, 1981, 831; *Arch. Pharm.*, 1974, 517; and S. W. Fox, et al., *J. Am. Chem. Soc.*, 1945, 496.

The process disclosed in WO 97/18813 may be summarized as illustrated in the following reaction scheme 1:

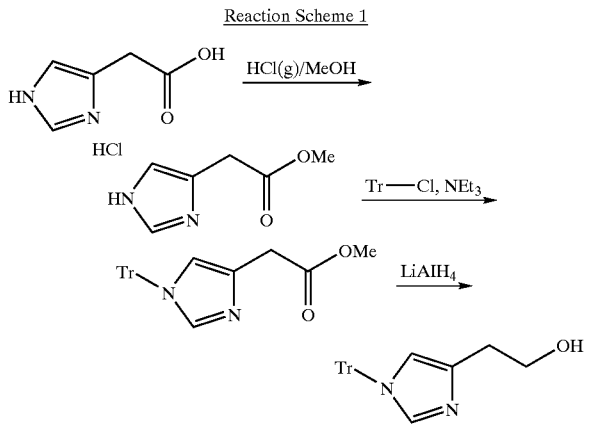

Reaction Scheme 1

In the above reaction scheme 1, Tr is a triphenylmethyl group.

In the process according to the reaction scheme 1, the starting material is relatively expensive and the reducing agent, lithium aluminum hydride (LiAlH$_4$), needs to be handled under an anhydrous condition. Accordingly, the process in accordance with the reaction scheme 1 has difficulties to be applied to an industrial-scale mass production.

The process disclosed in Holger Stark, et al., *J. Med. Chem.*, 1996, 39, 1220 may be summarized as illustrated in the following reaction scheme 2:

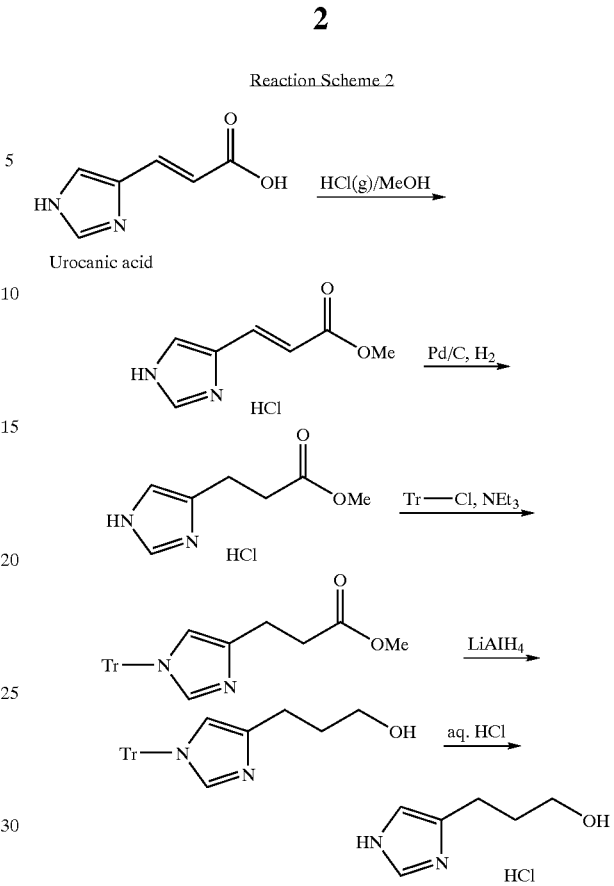

Reaction Scheme 2

In the above reaction scheme 2, Tr is a triphenylmethyl group.

The above process employs urocanic acid as a starting material, which is a very expensive reagent, and lithium aluminum hydride (LiAlH$_4$) as a reducing agent, which is unfavorable for industrial-scale mass production. Further, several complicated reactions are involved in the process. Accordingly, the process in accordance with the reaction scheme 2 has also difficulties to be applied to an industrial-scale mass production.

The process disclosed in G. A. A. Kivits. et al., *Heterocyclic chem.*, 1975, 12, 577 and Jurg R. Pfister, et al., *J. Heterocyclic Chem.*, 1981, 831 may be summarized as illustrated in the following reaction scheme 3:

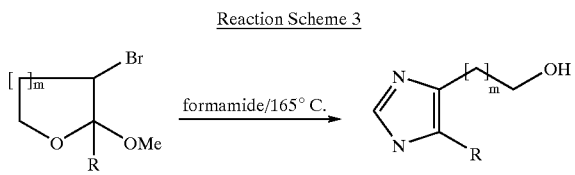

Reaction Scheme 3

In the above reaction scheme 3, R is hydrogen or methyl; m is 1 or 2.

The reaction, as shown in the reaction scheme 3, is carried out at a high temperature, such as 165° C., which causes degradation of the reactant and the product. Such degraded compounds may be changed into a tar, which makes it difficult to isolate and purify the product, thereby lowering the yield thereof. Further, the process employs formamide, thus, in order to remove un-reacted formamide remaining in the reaction system, multi-step isolation process, such as vacuum distillation, ion-exchange adsorption, and silica gel column chromatography, should be performed. Accordingly, the process in accordance with the reaction scheme 3 is difficult to apply to an industrial-scale mass production.

The process disclosed in *Arch. Pharm.*, 1974, 517 may be summarized as illustrated in the following reaction scheme 4:

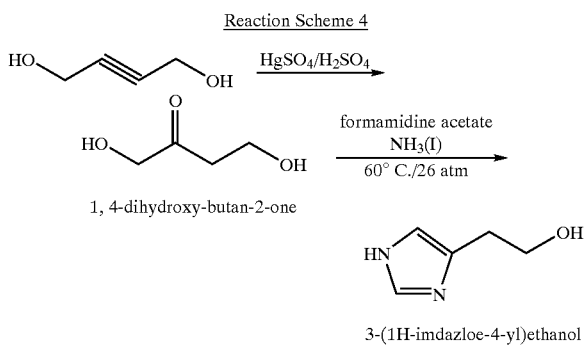

Reaction Scheme 4

1, 4-dihydroxy-butan-2-one 3-(1H-imdazloe-4-yl)ethanol

The process according to the reaction scheme 4 is relatively simple and the yield of the product is relatively moderate. However, mercury sulfate (II) ($HgSO_4$) for the preparation of 1,4-dihydroxy-butan-2-one is very toxic, which causes a serious problem in post-treatment. Further, the immidazole-cyclization step needs an additional high-pressure reactor.

The process disclosed in S. W. Fox, et al., *J. Am. Chem. Soc.*, 1945, 496 may be summarized as illustrated in the following reaction scheme 5:

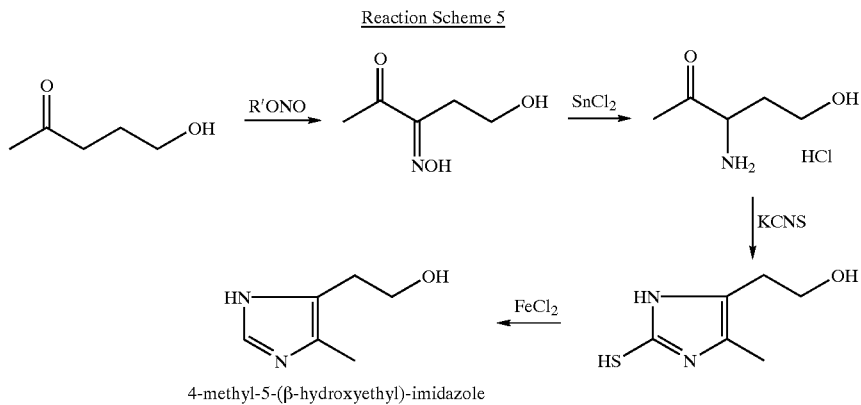

Reaction Scheme 5

4-methyl-5-(β-hydroxyethyl)-imidazole

In the above process according to the reaction scheme 5, the yield of oxime intermediate is very low (i.e. less than 10%), so that the yield of the final product, 4-methyl-5-(β-hydroxyethyl)imidazole, is also very low.

SUMMARY OF THE INVENTION

The present invention provides a process for preparing an imidazole derivative or its salt in high purity and yield under a mild condition, so as to be favorably applied to a large-scale mass production thereof.

In one aspect of the present invention, there is provided a process for preparing a compound of formula 1 or its salt, which comprises reacting a compound of formula 2 with formamidine or its salt in the presence of a base:

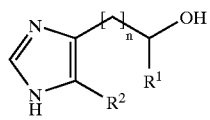

1

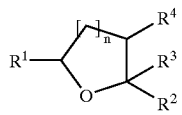

2 wherein, $R^1$ and $R^2$ are respectively hydrogen, $C_1$~$C_4$ alkyl, or a phenyl group; $R^3$ is an oxygen-containing leaving group or halogen; $R^4$ is halogen; and n is 1 or 2.

The above and other features and advantages of the present invention will become more apparent by describing in detail a preferred embodiment thereof.

DETAILED DESCRIPTION OF THE INVENTION

In the present invention, an imidzole derivative or its salt is prepared in high purity and yield by reacting a compound of formula 2 with formamidine or its salt in the presence of a base. The resulting compound may be further purified and isolated to give a compound of formula 1 or its salt.

The salt of the compound of formula 1 may be produced in the forms of an organic acid salt or an inorganic acid salt, e.g., in salt forms of hydrochloride, hydrobromide, sulfuric acid, sulfonic acid, acetic acid, maleic acid, oxalic acid, picric acid, salicylic acid, p-toluenesulfonic acid, or methansulfonic acid, etc.

The compound of formula 2, which is a starting material in the process of the present invention, may be prepared by a method which is known in the art (Cecilia H. Marzabadi, et al., *J. Org. Chem.*, 1993, 58, 3761~3766; Athelstan L. J. Beckwith, *J. Chem. Soc.* Perkin Trans, 1993, 1673; Emile M. Gaydou, *Tetrahedron Letters* No. 40, 4055~4058, 1972; M, Smietana, *Tetrahedron Letters*, 193~195, 2000; Shelton J. R., *J. Org. Chem.*, 1958, 23).

In the compound of formula 2, $R^3$ is halogen or an oxygen-containing leaving group. The oxygen-containing leaving group is a leaving group containing oxygen atom, such as hydroxy, acetoxy, methansulfonyloxy, p-toluensulfonyloxy, and etc.

The formamidine salt may be formamidine acetate or formamidine hydrochloride, which are commercially available. The amount of the formamidine or its salt is preferably about 1~10 eq., more preferably 2~5 eq., to 1 eq. of the compound of formula 2.

The base may be selected from the group consisting of a secondary amine, a tertiary amine, sodium acetate, sodium carbonate, sodium bicarbonate, potassium acetate, potassium carbonate, and potassium bicarbonate. The secondary amine includes diethylamine, 1,5-diazabicyclo[4,3,0]non-5-ene, and 1,8-diazabicyclo[5,4,0] undec-7-ene and the tertiary amine includes triethylamine, pyridine, and diisopropylethylamine. Among them, considering purity and yield of the product, diethylamine or potassium carbonate is preferable. The amount of the base is preferably about 2~5 eq. to 1 eq. of the compound of formula 2.

Although a reaction temperature in the process of the present invention is dependent on a reactant and a solvent employed, the reaction may be performed preferably at 70° C.~100° C., more preferably at 85° C.~95° C., considering purity and yield of the product. The reaction may be completed preferably in about 1~20 hours, more preferably about 2~6 hours.

The reaction of the present invention can be performed in the presence or absence of a solvent. For example, when a liquid base such as diethylamine is to be used, the reaction of the present invention can be performed without a solvent. When a solvent is to be used, examples of solvent include methanol, ethanol, isopropanol, acetone, acetonitrile, tetrahydrofuran, dichloromethane, ethyl acetate, 1,4-dioxane, toluene, 2-ethoxyethanol, ethylene glycol, N,N-dimethylformamide, and dimethylsulfoxide. Among them, considering solubility of formamidine salt and yield of the product, N,N-dimethylformamide or dimethylsulfoxide is preferable. The amount of the solvent is preferably about 5~20 times in volume, more preferably about 5~10 times in volume, based on the weight of the compound of the formula 2.

The process of the present invention may further include a step of distillation under a reduced-pressure so as to remove impurities and solvent having low boiling points.

The process of the present invention may further comprise a step of crystallization, for example by adding an acid in the presence of a solvent.

The acid for the crystallization may be selected according to a salt form of the product to be obtained. For example, by using hydrochloride, hydrobromide, sulfuric acid, acetic acid, maleic acid, oxalic acid, picric acid, salicylic acid, p-toluenesulfonic acid, or methansulfonic acid, the corresponding salts of the compound of formula 1 may be obtained. For example, when hydrochloride is used, the hydrochloride salt form of the compound of formula 1 is obtained. And, when oxalic acid is used, the oxalate form thereof is obtained.

The amount of the acid is preferably about 1~10 eq., more preferably 2~5 eq., to 1 eq. of the compound of formula 2.

The solvent used in the crystallization step includes methanol, ethanol, isopropanol, acetone, acetonitrile, tetrahydrofuran, diethylether, ethyl acetate, or a mixture thereof. Among them, methanol, ethanol, isopropanol, or acetone, which is able to crystallize the product in singular use, is preferable. The amount of the solvent may be the amount sufficient for dissolving the acid, e.g., about 2~20 times in volume, more preferably about 5~10 times in volume, based on the weight of the acid used.

The present invention is further illustrated and described by the following examples, which should not be taken to limit the scope of the invention.

EXAMPLE 1

The suspension of N-bromoacetamide (3.3 g) in water (1 ml) was cooled at 0° C. The solution of 3,4-dihydro-2H-pyran (2.0 g) in tetrahydrofuran (10 ml) was added dropwise thereto. The reaction mixture was stirred for 3 hours at 0° C. and concentrated under a reduced pressure to remove tetrahydrofuran. The resulting residue was diluted with dichloromethane (30 ml) and washed with water. The organic layer was dried and concentrated under a reduced pressure to give 3.5 g of 3-bromo-tetrahydropyran-2-ol as a pale yellow oil (yield: 81%).

$^1$H NMR (CDCl$_3$, 400 MHz) δ 4.93–4.74 (m, 1H), 4.33–4.28 (m, 0.5H), 3.72–3.50 (m, 1H), 4.16–3.96 (m, 2.5H), 2.54–1.50 (m, 4H)

EXAMPLE 2

The same procedures as described in Example 1 were repeated, except that 3.2 g of N-chlorosuccinimide instead of N-bromoacetamide was used, to give 2.65 g of 3-chloro-tetrahydropyran-2-ol (yield: 81%).

$^1$H NMR (CDCl$_3$, 400 MHz) δ 4.96–4.94 (m, 1H), 4.79–4.77 (m, 0.5H), 4.42–4.01 (m, 2.5H), 3.62–3.57 (m, 1H), 2.33–1.50 (m, 4H)

EXAMPLE 3

The same procedures as described in Example 1 were repeated, except that 5.4 g of N-iodosuccinimide instead of N-bromoacetamide was used, to give 4.65 g of 3-iodo-tetrahydropyran-2-ol (yield: 85%).

$^1$H NMR (CDCl$_3$, 400 MHz) δ 4.86–4.80 (d, 1H), 4.33–4.28 (m, 0.5H), 4.08–4.03 (m, 2.5H), 3.63–3.59 (m, 1H), 2.50–1.60 (m, 4H)

EXAMPLE 4

To the solution of N-bromosuccimide (4.5 g) in acetic acid (14.5 ml), was added dropwise 2.3 ml of 3,4-dihydro-2H-pyran at 10° C. The reaction mixture was diluted with 50 ml of diethyl ether and washed with 50 ml of water three times. The organic layer was washed with 1N NaHCO$_3$ solution, dried, and then concentrated under a reduced pressure to give 4.1 g of 2-acetoxy-3-bromo-tetrahydropyran as a colorless oil (yield: 73%).

$^1$H NMR (CDCl$_3$, 400 MHz) δ 5.87–5.84 (d, 1H), 4.06–3.91 (m, 1H), 3.80–3.68 (m, 1H), 2.50–2.32 (m, 1H), 2.13 (s, 3H), 2.1–1.88 (m, 3H), 1.72–1.50 (m, 1H)

EXAMPLE 5

The same procedures as described in Example 1 were repeated, except that 2.36 g of 2-methyl-3,4-dihydro-2H-pyran instead of 3,4-dihydro-2H-pyran was used, to give 3.28 g of 3-bromo-6-methyl-tetrahydropyran-2-ol (yield: 70%).

$^1$H NMR (CDCl$_3$, 400 MHz) δ 5.3(d, 1H), 4.33–4.28(m, 0.5H), 3.72–3.50(m, 1H), 4.16–3.96(m, 2.5H), 2.54–1.50(m, 4H)

EXAMPLE 6

The same procedures as described in Example 1 were repeated, except that 2.69 g of 2-ethyl-3,4-dihydro-2H-pyran instead of 3,4-dihydro-2H-pyran was used, to give 4.47 g of 3-bromo-6-ethyl-tetrahydropyran-2-ol (yield: 89%).

$^1$H NMR (CDCl$_3$, 400 MHz) δ 5.3 (d, 1H), 4.19 (d, 1H), 3.95–3.93 (m, 1H), 2.43–1.79 (m, 4H), 1.60–1.47 (m, 2H), 0.98–0.88 (m, 3H)

EXAMPLE 7

The same procedures as described in Example 1 were repeated, except that 1.68 g of 2,3-dihydrofuran instead of 3,4-dihydro-2H-pyran was used, to give 3.6 g of 3-bromo-tetrahydrofuran-2-ol (yield: 90%).

$^1$H NMR (CDCl$_3$, 400 MHz) δ 5.59 (m, 1H), 4.11–4.52 (m, 3H), 2.62–2.74 (m, 1H), 2.21–2.24 (m, 1H)

EXAMPLE 8

The same procedures as described in Example 1 were repeated, except that 2.02 g of 5-methyl-2,3-dihydrofuran instead of 3,4-dihydro-2H-pyran was used, to give 2.91 g of 3-bromo-2-methyl-tetrahydrofuran-2-ol (yield: 67%).

$^1$H NMR (CDCl$_3$, 400 MHz) δ4.55–4.58 (m, 1H), 3.74–3.85 (m, 2H), 2.40 (s, 3H), 2.18–2.30 (m, 1H), 2.09–2.12 (m, 1H)

EXAMPLE 9

The same procedures as described in Example 1 were repeated, except that 2.02 g of 2-methyl-2,3-dihydrofuran instead of 3,4-dihydro-2H-pyran was used, to give 3.04 g of 3-bromo-5-methyl-tetrahydrofuran-2-ol (yield: 70%).

$^1$H NMR (CDCl$_3$, 400 MHz) δ 5.56 (d, 1H), 4.60–4.54 (m, 1H), 4.27 (d, 1H), 2.81 (d, 1H), 2.35–2.25 (m, 2H), 1.40 (d, 3H)

EXAMPLE 10

The same procedures as described in Example 1 were repeated, except that 3.51 g of 2-phenyl-2,3-dihydrofuran instead of 3,4-dihydro-2H-pyran was used, to give 4.90 g of 3-bromo-5-phenyl-tetrahydrofuran-2-ol (yield: 84%).

$^1$H NMR (CDCl$_3$, 400 MHz) δ 7.43–7.30 (m, 5H), 5.68–5.67 (d, 1H), 5.45–5.41 (m, 1H), 4.34–4.32 (d, 1H), 3.49 (d, 1H), 2.64–2.52 (m, 2H)

EXAMPLE 11

5.0 g of 3-bromo-tetrahydropyran-2-ol prepared in Example 1 and 5.75 g of formamidine acetate were added to 25 ml of N,N-dimethylformamide and 9 ml of diethylamine was added dropwise thereto. The reaction mixture was stirred for about 4 hours at 80° C. and distilled in vacuo for about 1 hour at the same temperature to remove the solvent. The resulting oily residue was diluted with 25 ml of acetone and 4.97 g of oxalic acid was slowly added thereto for crystallization. The reaction mixture was stirred for about 1 hour, filtered, and washed with acetone to give 2.5 g of 3-(1H-imidazol-4-yl)propanol oxalate (yield: 42%).

$^1$H NMR (D$_2$O, 400 MHz) δ 8.53 (s, 1H), 7.20 (s, 1H), 3.60 (t, J=6.4 Hz 2H 2.76 (t, J=7.6 Hz 2H), 1.87 (m, 2H)

EXAMPLE 12

The same procedures as described in Example 11 were repeated, except that N,N-dimethylformamide was not used, to give 2.39 g of 3-(1 H-imidazol-4-yl)propanol oxalate (yield: 40%).

EXAMPLE 13

The same procedures as described in Example 11 were repeated, except that potassium carbonate (9.54 g) instead of diethylamine was used, to give 2.1 g of 3-(1 H-imidazol-4-yl)propanol oxalate (yield: 35%).

EXAMPLE 14

The same procedures as described in Example 11 were repeated, except that isopropanol (35 ml) instead of acetone was used, to give 2.15 g of 3-(1H-imidazol-4-yl)propanol oxalate (yield: 36%).

EXAMPLE 15

The same procedures as described in Example 11 were repeated, except that 6.16 g of 2-acetoxy-3-bromo-tetrahydropyran prepared in Example 4 instead of 3-bromo-tetrahydropyran-2-ol was used, to give 2.11 g of 3-(1H-imidazol-4-yl)propanol oxalate (yield: 35%).

EXAMPLE 16

The same procedures as described in Example 11 were repeated, except that 3.77 g of 3-chloro-tetrahydropyran-2-ol prepared in Example 2 instead of 3-bromo-tetrahydropyran-2-ol was used, to give 2.33 g of 3-(1H-imidazol-4-yl)propanol oxalate (yield: 39%).

EXAMPLE 17

The same procedures as described in Example 11 were repeated, except that 6.29 g of 3-iodo-tetrahydropyran-2-ol prepared in Example 3 instead of 3-bromo-tetrahydropyran-2-ol was used, to give 2.04 g of 3-(1H-imidazol-4-yl)propanol oxalate (yield: 34%).

EXAMPLE 18

The same procedures as described in Example 11 were repeated, except that 4.45 g of formamidine hydrochloride instead of formamidine acetate was used, to give 2.17 g of 3-(1H-imidazole-4-yl)propanol oxalate (yield: 36%).

EXAMPLE 19

3.74g of formamidine acetate was added to 3.0 g of 3-bromo-tetrahydrofuran-2-ol prepared in Example 7. 3.94 g of diethylamine was slowly added to the reaction mixture, which was then stirred for about 4 hours at 80° C. and distilled in vacuo for about 1 hour at the same temperature. The resulting oily residue was diluted with 15ml of ethanol and insoluble material was filtered off. Ethanolic hydrogen chloride was added to the reaction mixture, which was then stirred for about 1 hour. The resulting solid was filtered and washed with ethanol to give 1.02 g of 3-(1H-imidazol-4-yl) ethanol hydrochloride (yield: 38%).

$^1$H -NMR (DMSO-d$_6$, 400 MHz) δ 7.49 (s, 1H), 6.74 (s, 1H), 4.67 (br, 1H), 3.58 (t, J=7.2 Hz 2H), 2.64 (t, J=7.2 Hz 2H)

EXAMPLE 20

The same procedures as described in Example 19 were repeated, except that N,N-dimethylformamide (15 ml) was used as a solvent, to give 0.88 g of 3-(1H-imidazol-4-yl) ethanol hydrochloride (yield: 33%).

EXAMPLE 21

The same procedures as described in Example 19 were repeated, except that potassium carbonate (6.18 g) instead of diethylamine was used, to give 0.99 g 3-(1H-imidazol-4-yl) ethanol hydrochloride (yield: 37%).

EXAMPLE 22

5.0 g of 3-bromo-2-methyl-tetrahydrofuran-2-ol and 5.75 g of formamidine acetate were added to 15 ml of N,N-dimethylformamide. 5 g of diethylamine was slowly added to the reaction mixture, which was then stirred for about 4 hours at 80° C. and was distilled in vacuo for about 1 hour at the same temperature. The resulting oily residue was diluted with 25 ml of acetone. 4.95 g of oxalic acid was added to the reaction mixture, which was then stirred for about 1 hour. The resulting solid was filtered and washed with acetone to give 2.5 g of 2-(5-methyl-1H-imidazol-4-yl)ethanol oxalate (yield: 42%).

$^1$H -NMR (DMSO-d$_6$, 400 MHz) δ 8.83 (s, 1H), 4.85 (br, 1H), 3.59 (t, J=6.4 Hz 2H), 2.71 (t, J=6.4 Hz 2H), 2.21 (s, 3H)

EXAMPLE 23

The same procedures as described in Example 22 were repeated, except that N,N-dimethylformamide was not used, to give 2.32 g of 2-(5-methyl-1H-imidazol-4-yl)ethanol oxalate (yield: 39%).

EXAMPLE 24

The same procedures as described in Example 22 were repeated, except that potassium carbonate (9.54 g) instead of diethylamine was used, to give 1.95 g of 2-(5-methyl-1H-imidazol-4-yl)ethanol oxalate (yield: 33%).

EXAMPLE 25

The same procedures as described in Example 22 were repeated, except that isopropanol (35 ml) instead of acetone was used, to give 2.13 g of 2-(5-methyl-1H-imidazol-4-yl) ethanol oxalate (yield: 36%).

EXAMPLE 26

5.2 g of formamidine acetate was added to 6.08 g of 3-bromo-5-phenyl-tetrahydrofuran-2-ol prepared in Example 10. 16 ml of diethylamine was added to the reaction mixture, which was then stirred for about 3 hours at 80° C. and distilled in vacuo for about 1 hour at the same temperature. The resulting oily residue was diluted with 30 ml of acetone. 4.5 g of oxalic acid was added to the reaction mixture, which was then stirred for about 1 hour. The resulting solid was filtered and washed with acetone to give 2.9 g of 2-(1H-imidazol-4-yl)-1-phenyl-ethanol oxalate (yield: 42%).

$^1$H -NMR (DMSO-d$_6$, 400 MHz) δ 8.53 (s, 1H), 7.11–7.43 (m, 5H), 6.87. (s, 1H), 4.82–4.86 (m, 1H), 2.85–2.97 (m, 2H)

EXAMPLE 27

The same procedures as described in Example 26 were repeated, except that N,N-dimethylformamide (20 ml) was used as a solvent, to give 2.43 g of 2-(1H-imidazol-4-yl)-1-phenyl-ethanol oxalate (yield: 35%).

EXAMPLE 28

The same procedures as described in Example 26 were repeated, except that potassium carbonate (8.64 g) instead of diethylamine was used, to give 2.6 g of 2-(1H-imidazol-4-yl)-1-phenyl-ethanol oxalate (yield: 37%).

EXAMPLE 29

The same procedures as described in Example 26 were repeated, except that isopropanol (32 ml) instead of acetone was used, to give 2.13 g of 2-(1H-imidazol-4-yl)-1-phenyl-ethanol oxalate (yield: 31%).

EXAMPLE 30

5.2 g of formamidine acetate was added to 4.5 g of 3-bromo-5-methyl-tetrahydrofuran-2-ol prepared in Example 9. 16 ml of diethylamine was added to the reaction mixture, which was then stirred for about 2.5 hours at 80° C. and distilled in vacuo for about 1 hour at the same temperature. The resulting oily residue was diluted with 32 ml of acetone. 13.5 g of oxalic acid was added to the reaction mixture, which was then stirred for about 1 hour. The resulting solid was filtered and washed with acetone to give 2.9 g of 1-(1H-imidazol-4-yl)-propan-2-ol oxalate (yield: 54%).

$^1$H-NMR (DMSO-d$_6$, 400 MHz) δ 8.92 (s, 1H), 7.34 (s, 1H), 3.84–3.89 (m, 1H), 2.58–2.73 (m, 2H), 1.05–1.06 (d, J=Hz 3H)

EXAMPLE 31

3.2 g of formamidine acetate was added to 3.0 g of 3-bromo-6-methyl-tetrahydropyran-2-ol prepared in Example 5. 3.29 g of diethylamine was added to the reaction mixture, which was then stirred for about 3 hours at 80° C. and distilled in vacuo for about 1 hour at the same temperature. The resulting oily residue was diluted with 15 ml of acetone. 4.05 g of oxalic acid was added to the reaction mixture which was then stirred for about 1 hour. The resulting solid was filtered and washed with methanol to give 1.38 g of 4-(1H-imidazole-4-yl)-buthan-2-ol oxalate (yield: 40%).

$^1$H-NMR (DMSO-d$_6$, 400 MHz) δ 8.88 (s, 1H), 7.36 (s, 1H), 3.57–3.76 (m, 1H), 2.62–2.71 (m, 2H), 1.58–1.65 (m, 2H), 1.05–1.07 (d, 3H)

EXAMPLE 32

4.48 g of formamidine acetate was added to 4.5 g of 3-bromo-6-ethyl-tetrahydropyran-2-ol prepared in Example 6. 3.9 g of diethylamine was added to the reaction mixture, which was then stirred for about 3 hours at 80° C. and distilled in vacuo for about 1 hour at the same temperature. The resulting oily residue was diluted with 25 ml of acetone. 5.8 g of oxalic acid was added to the reaction mixture, which was then stirred for about 1 hour. The resulting solid was filtered and washed with methanol to give 1.89 g of 1-(1H-imidazole-4-yl)-pentan-3-ol oxalate (yield: 36%).

$^1$H-NMR (DMSO-d$_6$, 400 MHz) δ 8.39 (s, 1H), 7.12 (s, 1H), 3.29–3.35 (m, 1H), 2.55–2.74 (m, 2H), 1.51–1.76 (m, 2H), 1.25–1.42 (m, 2H), 0.82–0.86 (t, 3)

While this invention has been particularly shown and described with reference to preferred embodiments thereof, it will be understood by those skilled in the art that various changes in form and details may be made therein without departing from the spirit and scope of the invention as defined by the appended claims.

What is claimed is:

1. A process for preparing a compound of formula 1 or its salt, which comprises reacting a compound of formula 2 with formamidine or its salt in the presence of a base:

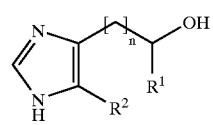

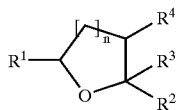

wherein $R^1$ and $R^2$ are respectively hydrogen, $C_1$~$C_4$ alkyl, or a phenyl group; $R^3$ is an oxygen-containing leaving group or halogen; $R^4$ is halogen; and n is 1 or 2.

2. The process of claim 1, wherein the formamidine salt is formamidine acetate or formamidine hydrochloride.

3. The process of claim 1, wherein the formamidine or its salt is reacted with the compound of formula 2 in an equivalent ratio of 1:1 to 10:1.

4. The process of claim 1, wherein the base is selected from the group consisting of a secondary amine, a tertiary amine, sodium acetate, sodium carbonate, sodium bicarbonate, potassium acetate, potassium carbonate, and potassium bicarbonate.

5. The process of claim 1, wherein the base is added in 2~5 eq. to 1 eq. of the compound of formula 2.

6. The process of claim 1, wherein the reaction is carried out at 70° C.~100° C.

7. The process of claim 1, wherein the reaction is carried out in the presence of a solvent.

8. The process of claim 7, wherein the solvent is selected from the group consisting of methanol, ethanol, isopropanol, acetone, acetonitrile, tetrahydrofuran, dichloromethane, ethyl acetate, 1,4-dioxane, toluene, 2-ethoxyethanol, ethylene glycol, N,N-dimethylformamide, and dimethylsulfoxide.

9. The process of claim 1, further comprising adding an acid in the presence of a solvent.

10. The process of claim 9, wherein the acid is added in 1~10 eq. to 1 eq. of the compound of formula 2.

11. The process of claim 9, wherein the solvent is selected from the group consisting of methanol, ethanol, isopropanol, acetone, acetonitrile, tetrahydrofuran, diethylether, ethyl acetate and a mixture thereof.

12. The process of claim 9, wherein the acid is oxalic acid.

* * * * *